(12) United States Patent
Miyama

(10) Patent No.: US 9,272,267 B2
(45) Date of Patent: Mar. 1, 2016

(54) CATALYST FOR OXYGENATE SYNTHESIS AND METHOD FOR MANUFACTURING SAME, DEVICE FOR MANUFACTURING OXYGENATE, AND METHOD FOR MANUFACTURING OXYGENATE

(75) Inventor: Toshihito Miyama, Tsukuba (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 40 days.

(21) Appl. No.: 14/237,427

(22) PCT Filed: Aug. 22, 2012

(86) PCT No.: PCT/JP2012/071179
§ 371 (c)(1),
(2), (4) Date: Feb. 6, 2014

(87) PCT Pub. No.: WO2013/031598
PCT Pub. Date: Mar. 7, 2013

(65) Prior Publication Data
US 2014/0187654 A1  Jul. 3, 2014

(30) Foreign Application Priority Data

Aug. 31, 2011  (JP) ................ 2011-189052
Aug. 31, 2011  (JP) ................ 2011-189053
Aug. 31, 2011  (JP) ................ 2011-189056
Feb. 24, 2012  (JP) ................ 2012-039007
Feb. 24, 2012  (JP) ................ 2012-039008
Feb. 24, 2012  (JP) ................ 2012-039009

(51) Int. Cl.
| | |
|---|---|
| *B01J 31/00* | (2006.01) |
| *B01J 23/00* | (2006.01) |
| *B01J 23/656* | (2006.01) |
| *C07C 29/158* | (2006.01) |
| *C07C 45/49* | (2006.01) |
| *B01J 37/02* | (2006.01) |
| *B01J 21/14* | (2006.01) |

(52) U.S. Cl.
CPC .......... *B01J 23/6562* (2013.01); *B01J 37/0207* (2013.01); *C07C 29/158* (2013.01); *C07C 45/49* (2013.01); *B01J 21/14* (2013.01); *B01J 37/02* (2013.01); *B01J 37/0242* (2013.01); *Y02E 50/18* (2013.01); *Y02P 20/52* (2015.11)

(58) Field of Classification Search
CPC ........ B01J 21/14; B01J 37/0242; B01J 37/02; B01J 23/6552
USPC ................... 502/104, 302, 313, 324
See application file for complete search history.

(56) References Cited

U.S. PATENT DOCUMENTS

| | | | |
|---|---|---|---|
| 4,235,798 A | 11/1980 | Bartley et al. | |
| 4,758,600 A | 7/1988 | Arimitsu et al. | |
| 2002/0037938 A1* | 3/2002 | Luo et al. | 518/716 |

FOREIGN PATENT DOCUMENTS

| | | | |
|---|---|---|---|
| CN | 1724151 | | 1/2006 |
| EP | 0 021 443 | | 1/1981 |
| JP | 57-062230 | * | 4/1982 |
| JP | 57062230 | | 4/1982 |
| JP | 59-78130 | | 5/1984 |
| JP | 60-32733 | | 2/1985 |
| JP | 61-36730 | | 8/1986 |
| JP | 61-36731 | | 8/1986 |
| JP | 1-294643 | | 11/1989 |
| JP | 2001-31602 | | 2/2001 |
| WO | 2006/123146 | | 11/2006 |
| WO | 2010/092819 | | 8/2010 |
| WO | 2011/053953 | | 5/2011 |

OTHER PUBLICATIONS

International Search Report issued Oct. 23, 2012 in International (PCT) Application No. PCT/JP2012/071179.
Schwartz et al., "EXAFS and FT-IR Characterization of Mn and Li Promoted Titania-Supported Rh Catalysts for CO Hydrogenation", ACS Catalysis, vol. 1, No. 10, Aug. 22, 2011, pp. 1298-1306.
Wang et al., "Different Mechanisms for the Formation of Acetaldehyde and Ethanol on the Rh-Based Catalysts", Journal of Catalysts. vol. 196, No. 1, Nov. 15, 2000, pp. 46-55.
Mo et al., "La, V, and Fe promotion of Rh/$SiO_2$ for CO hydrogenation: Effect on adsorption and reaction", Journal of Catalysis, vol. 267, No. 2, Sep. 16, 2009, pp. 167-176.
Mei et al., "Ethanol synthesis from syngas over Rh-based/$SiO_2$ catalysts: A combined experimental and theoretical modeling study", Journal of Catalysis, vol. 271, No. 2, Mar. 19, 2010, pp. 325-342.
Kusama et al., "$CO_2$ hydrogenation to ethanol over promoted Rh/$SiO_2$ catalysts", Catalysis Today, vol. 28, No. 3, May 25, 1996, pp. 261-266.
Burch et al., "Investigation of the synthesis of oxygenates from carbon monoxide/hydrogen mixtures on supported rhodium catalysts", Applied Catalysis A: General, vol. 88, No. 1, Sep. 1, 1992, pp. 39-60.
Extended European Search Report issued Jul. 6, 2015 in European Application No. 12827075.8.
Office Action issued Sep. 17, 2015 in corresponding Chinese Application No. 201280041639.3, with English translation.

* cited by examiner

*Primary Examiner* — Jafar Parsa
(74) *Attorney, Agent, or Firm* — Wenderoth, Lind & Ponack, L.L.P.

(57) ABSTRACT

The present invention relates to a catalyst for oxygenate synthesis for synthesizing an oxygenate from a mixed gas containing hydrogen and carbon monoxide, the catalyst for oxygenate synthesis containing: a component (A): rhodium, a component (B): manganese, a component (C): an alkali metal, and a component (D): a component (D1), component (D2) or component (D3), wherein the component (D1) is one or more substances selected from the group consisting of titanium, vanadium and chromium, the component (D2) is an element belonging to group 13 of the periodic table, and the component (D3) is one or more substances selected from the group consisting of magnesium and lanthanoids. According to the present invention, an oxygenate can be synthesized efficiently from a mixed gas containing hydrogen and carbon monoxide.

8 Claims, 1 Drawing Sheet

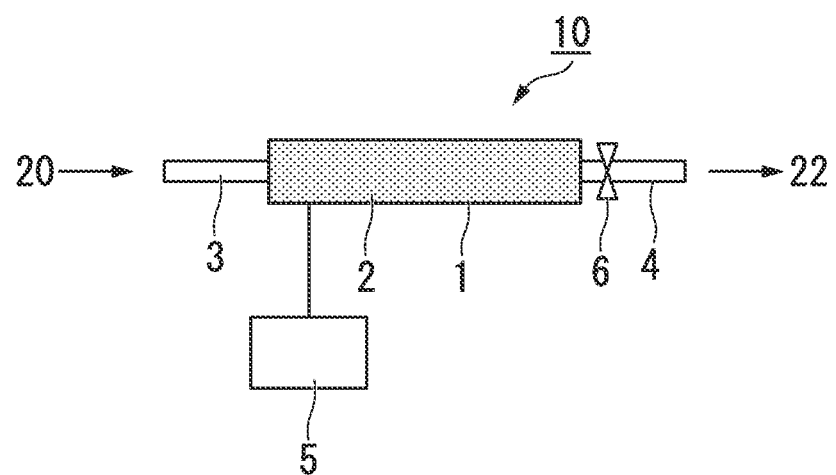

CATALYST FOR OXYGENATE SYNTHESIS AND METHOD FOR MANUFACTURING SAME, DEVICE FOR MANUFACTURING OXYGENATE, AND METHOD FOR MANUFACTURING OXYGENATE

TECHNICAL FIELD

The present invention relates to a catalyst for oxygenate synthesis and a method for manufacturing the same, a device for manufacturing an oxygenate, and a method for manufacturing an oxygenate. Priority is claimed on Japanese Patent Application No. 2011-189052, Japanese Patent Application No. 2011-189053 and Japanese Patent Application No. 2011-189056, filed Aug. 31, 2011, and Japanese Patent Application No. 2012-039007, Japanese Patent Application No. 2012-039008 and Japanese Patent Application No. 2012-039009, filed Feb. 24, 2012, the contents of which are incorporated herein by reference.

BACKGROUND ART

Bioethanol is becoming more widespread as an alternative fuel to petroleum. Bioethanol is mainly manufactured by the saccharification and fermentation of sugar cane or maize. In recent years, techniques have been developed for manufacturing bioethanol from wood-based or plant-based biomass (also known as cellulose-based biomass), including the unused portions of crops such as waste wood or rice straw, which are not in competition for use as foodstuffs or animal feed.

In order to use a cellulose-based biomass as a raw material, and enable the manufacture of bioethanol using a conventional ethanol fermentation method, the cellulose must be saccharified. Examples of the saccharification method include a concentrated sulfuric acid saccharification method, a dilute sulfuric acid-enzymatic saccharification method, and a heated water saccharification method, but many problems still remain to manufacturing bioethanol inexpensively.

On the other hand, another method exists in which the cellulose-based biomass is converted to a mixed gas containing hydrogen and carbon monoxide, and ethanol is then synthesized from this mixed gas. With this method, tests are being conducted with the aim of manufacturing bioethanol efficiently from cellulose-based biomass that is difficult to use in the ethanol fermentation method. In addition, this method is not limited to wood-based and plant-based biomass, but can use various manners of biomass as the raw material, including animal-based biomass derived from animal corpses and feces, raw garbage, waste paper and waste fiber.

Moreover, the mixed gas of hydrogen and carbon monoxide can also be obtained from resources besides petroleum, including natural gas and coal, and therefore methods of synthesizing oxygenates from this type of mixed gas are also being researched as potential techniques for breaking away from petroleum dependency.

Examples of known methods for obtaining oxygenates such as ethanol, acetaldehyde and acetic acid from a mixed gas of hydrogen and carbon monoxide include methods in which, for example, the mixed gas is brought into contact with a catalyst containing rhodium, an alkali metal and manganese (for example, see Patent Documents 1 and 2).

DOCUMENTS OF RELATED ART

Patent Documents

Patent Document 1: Japanese Examined Patent Application, Second Publication No. Sho 61-36730
Patent Document 2: Japanese Examined Patent Application, Second Publication No. Sho 61-36731

SUMMARY OF THE INVENTION

Problems to be Solved by the Invention

However, it is desirable that the catalysts used for synthesizing oxygenates are able to synthesize the oxygenates with greater efficiency.

Further, in the methods described in Patent Documents 1 and 2, oxygenate synthesis methods in which the CO conversion rate is 25% or less are disclosed, but a catalyst for oxygenate synthesis is required which does not cause an excessive reduction in the selectivity for the produced ethanol even if the CO conversion rate is 25% or greater.

Accordingly, an object of the present invention is to provide a catalyst for oxygenate synthesis which is capable of efficiently synthesizing an oxygenate from a mixed gas of hydrogen and carbon monoxide.

Means to Solve the Problems

The present invention relates to the following aspects.
[1] A catalyst for oxygenate synthesis for synthesizing an oxygenate from a mixed gas containing hydrogen and carbon monoxide, the catalyst for oxygenate synthesis containing:
a component (A): rhodium, a component (B): manganese, a component (C): an alkali metal, and a component (D): a component (D1), component (D2) or component (D3), wherein
the component (D1) is one or more substances selected from the group consisting of titanium, vanadium and chromium, the component (D2) is an element belonging to group 13 of the periodic table, and the component (D3) is one or more substances selected from the group consisting of magnesium and lanthanoids.
[2] The catalyst for oxygenate synthesis according to [1], wherein the catalyst for oxygenate synthesis is represented by formula (I) shown below:

$$aA \cdot bB \cdot cC \cdot dD \quad (I)$$

wherein A represents the component (A), B represents the component (B), C represents the component (C), D represents the component (D), and each of a, b, c and d represents a molar fraction, wherein
$a+b+c+d=1$,
$a=0.05$ to $0.98$,
$b=0.0005$ to $0.67$,
$c=0.0005$ to $0.51$, and
$d=0.002$ to $0.95$.
[3] The catalyst for oxygenate synthesis according to [1] or [2], wherein the component (D) is the component (D1): one or more substances selected from the group consisting of titanium, vanadium and chromium.
[4] The catalyst for oxygenate synthesis according to [1] or [2], wherein the component (D) is the component (D2): one or more substances selected from among elements belonging to group 13 of the periodic table.
[5] The catalyst for oxygenate synthesis according to [1] or [2], wherein the component (D) is the component (D3): one or more substances selected from the group consisting of magnesium and lanthanoids.
[6] The catalyst for oxygenate synthesis according to [2] or [3], wherein a, b, c and d in the formula (I) satisfy the conditions shown below:
$a+b+c+d=1$,
$a=0.053$ to $0.98$,
$b=0.0006$ to $0.67$,
$c=0.00056$ to $0.51$, and
$d=0.0024$ to $0.94$.

[7] The catalyst for oxygenate synthesis according to [2] or [4], wherein a, b, c and d in the formula (I) satisfy the conditions shown below:
a+b+c+d=1,
a=0.053 to 0.98,
b=0.00059 to 0.67,
c=0.00056 to 0.51, and
d=0.0024 to 0.95.

[8] The catalyst for oxygenate synthesis according to [2] or [5], wherein a, b, c and d in the formula (I) satisfy the conditions shown below:
a+b+c+d=1,
a=0.065 to 0.98,
b=0.00075 to 0.67,
c=0.0007 to 0.51, and
d=0.0024 to 0.93.

[9] The catalyst for oxygenate synthesis according to any one of [1] to [8], wherein the components (A) to (D) are supported on a carrier.

[10] The catalyst for oxygenate synthesis according to any one of [1], [2], [3], [6] or [9], wherein the components (A) to (D1) are supported on a carrier.

[11] The catalyst for oxygenate synthesis according to any one of [1], [2], [4], [7] or [9], wherein the components (A) to (D2) are supported on a carrier.

[12] The catalyst for oxygenate synthesis according to any one of [1], [2], [5], [8] or [9], wherein the components (A) to (D3) are supported on a carrier.

[13] A method for manufacturing the catalyst for oxygenate synthesis according to [9], the method including:
supporting the component (D) on the carrier to form a primary support body, bringing an alkaline aqueous solution into contact with the primary support body, and subsequently supporting the components (A) to (C) on the primary support body.

[14] A method for manufacturing the catalyst for oxygenate synthesis according to [10] the method including:
supporting the component (D1) on the carrier to form a primary support body, bringing an alkaline aqueous solution into contact with the primary support body, and subsequently supporting the components (A) to (C) on the primary support body.

[15] A method for manufacturing the catalyst for oxygenate synthesis according to [11], the method including:
supporting the component (D2) on the carrier to form a primary support body, bringing an alkaline aqueous solution into contact with the primary support body, and subsequently supporting the components (A) to (C) on the primary support body.

[16] A method for manufacturing the catalyst for oxygenate synthesis according to [12], the method including:
supporting the component (D3) on the carrier to form a primary support body, bringing an alkaline aqueous solution into contact with the primary support body, and subsequently supporting the components (A) to (C) on the primary support body.

[17] A device for manufacturing an oxygenate, the device including:
a reaction tube packed with the catalyst for oxygenate synthesis according to any one of [1] to [12];
a supply unit for supplying the mixed gas into the reaction tube; and
a discharge unit for discharging the product from the reaction tube.

[18] A method for manufacturing an oxygenate, wherein an oxygenate is obtained by bringing a mixed gas containing hydrogen and carbon monoxide into contact with the catalyst for oxygenate synthesis according to any one of [1] to [12].

[19] The catalyst for oxygenate synthesis according to any one of [1] to [12], wherein the oxygenate is one or more substances selected from the group consisting of acetic acid, ethanol, acetaldehyde, methanol, propanol, methyl formate, ethyl formate, methyl acetate and ethyl acetate.

[20] The catalyst for oxygenate synthesis according to any one of [13] to [16] or [18], wherein the oxygenate is one or more substances selected from the group consisting of acetic acid, ethanol, acetaldehyde, methanol, propanol, methyl formate, ethyl formate, methyl acetate and ethyl acetate.

[21] The device for manufacturing an oxygenate according to [17], wherein the oxygenate is one or more substances selected from the group consisting of acetic acid, ethanol, acetaldehyde, methanol, propanol, methyl formate, ethyl formate, methyl acetate and ethyl acetate.

In the present description, an oxygenate describes a molecule composed of carbon, hydrogen and oxygen atoms, and examples include acetic acid, ethanol, acetaldehyde, methanol, propanol, methyl formate, ethyl formate, methyl acetate and ethyl acetate.

Effects of the Invention

The catalyst for oxygenate synthesis according to the present invention can efficiently synthesize an oxygenate from a mixed gas of hydrogen and carbon monoxide.

BRIEF DESCRIPTION OF THE DRAWING

FIG. 1 is a schematic view of a device for manufacturing an oxygenate according to an embodiment of the present invention.

EMBODIMENTS FOR CARRYING OUT THE INVENTION (Catalyst for Oxygenate Synthesis)

A catalyst for oxygenate synthesis according to the present invention (hereafter also referred to as simply "the catalyst") contains a component (A): rhodium, a component (B): manganese, a component (C): an alkali metal, and a component (D): a component (D1), component (D2) or component (D3).

The component (D1) is one or more substances selected from the group consisting of titanium, vanadium and chromium, the component (D2) is an element belonging to group 13 of the periodic table, and the component (D3) is one or more substances selected from the group consisting of magnesium and lanthanoids.

By including the components (A) to (D), the components (A) to (D1), the components (A) to (D2) or the components (A) to (D3), an oxygenate can be synthesized with good efficiency.

The component (C) is an alkali metal. Examples of the component (C) include lithium (Li), sodium (Na), potassium (K), rubidium (Rb) and cesium (Cs). Among these, lithium is preferred, as it enables the generation of by-products to be reduced and yields a higher CO conversion rate, meaning the oxygenate can be synthesized more efficiently. The term "CO conversion rate" means "the percentage indicating the number of moles of CO consumed among the total number of moles of CO within the mixed gas".

The component (D) is any one of the component (D1), the component (D2) and the component (D3).

The component (D1) is one or more substances selected from the group consisting of titanium (Ti), vanadium (V) and chromium (Cr). As the component (D1), titanium or vanadium is preferable, and titanium is more preferable. By including the component (D1), the catalyst is able to efficiently synthesize the oxygenate, and the amount of ethanol within the oxygenate can also be increased. The mechanism by which including the component (D1) enhances the efficiency of the oxygenate synthesis and increases the amount of ethanol within the oxygenate is not entirely clear, but it is thought that including the component (D1) enhances the dispersibility of the components (A) to (C).

The component (D2) is an element belonging to group 13 of the periodic table. Examples of the component (D2) include boron (B), aluminum (Al), gallium (Ga), indium (In) and thallium (Tl). Among these, boron or aluminum is preferable, and boron is more preferable. By including the component (D2), the catalyst is able to efficiently synthesize the oxygenate. The mechanism by which including the component (D2) enhances the efficiency of the oxygenate synthesis is not entirely clear, but it is thought that including the component (D2) enhances the dispersibility of the components (A) to (C).

The component (D3) is one or more substances selected from the group consisting of magnesium and lanthanoids. The lanthanoids are the elements from atomic numbers 51 to 71, namely from lanthanum to ruthenium (Lu), such as lanthanum (La), cerium (Ce) and praseodymium (Pr). As the component (D3), magnesium or lanthanum is preferable. By including the component (D3), the catalyst is able to efficiently synthesize the oxygenate, and the amount of ethanol within the oxygenate can also be increased.

The mechanism by which including the component (D3) enhances the efficiency of the oxygenate synthesis and increases the amount of ethanol within the oxygenate is not entirely clear, but it is thought that including the component (D3) enhances the dispersibility of the components (A) to (C).

The catalyst of the present invention preferably has a composition represented by formula (I) shown below.

$$aA \cdot bB \cdot cC \cdot dD \quad (I)$$

In formula (I), A represents the component (A), B represents the component (B), C represents the component (C), D represents the component (D), and each of a, b, c and d represents a molar fraction, wherein a+b+c+d=1,
a=0.05 to 0.98,
b=0.0005 to 0.67,
c=0.0005 to 0.51, and
d=0.002 to 0.95.

When the component (D) is the component (D1): one or more substances selected from the group consisting of titanium, vanadium and chromium, the value of a in formula (I) is preferably from 0.053 to 0.98. If a is less than the aforementioned lower limit, then the amount of the component (A) is too small, and there is a possibility that the efficiency of the oxygenate synthesis may not be enhanced sufficiently, whereas if a exceeds the aforementioned upper limit, then the amounts of the components (B) to (D) become too small, and there is a possibility that the efficiency of the oxygenate synthesis may not be enhanced sufficiently.

When the component (D) is the component (D1): one or more substances selected from the group consisting of titanium, vanadium and chromium, the value of b in formula (I) is preferably from 0.0006 to 0.67. If b is less than the aforementioned lower limit, then the amount of the component (B) is too small, and there is a possibility that the efficiency of the oxygenate synthesis may not be enhanced sufficiently, whereas if b exceeds the aforementioned upper limit, then the amounts of the component (A), the component (C) and the component (D1) become too small, and there is a possibility that the efficiency of the oxygenate synthesis may not be enhanced sufficiently.

When the component (D) is the component (D1): one or more substances selected from the group consisting of titanium, vanadium and chromium, the value of c in formula (I) is preferably from 0.00056 to 0.51. If c is less than the aforementioned lower limit, then the amount of the component (C) is too small, and there is a possibility that the efficiency of the oxygenate synthesis may not be enhanced sufficiently, whereas if c exceeds the aforementioned upper limit, then the amounts of the component (A), the component (B) and the component (D1) become too small, and there is a possibility that the efficiency of the oxygenate synthesis may not be enhanced sufficiently.

When the component (D) is the component (D1): one or more substances selected from the group consisting of titanium, vanadium and chromium, the value of d in formula (I) is preferably from 0.0024 to 0.94. If d is less than the aforementioned lower limit, then the amount of the component (D1) is too small, and there is a possibility that the efficiency of the oxygenate synthesis may not be enhanced sufficiently, whereas if d exceeds the aforementioned upper limit, then the amounts of the components (A) to (C) become too small, and there is a possibility that the efficiency of the oxygenate synthesis may not be enhanced sufficiently.

When the component (D1) is titanium, the value of a in formula (I) is preferably from 0.053 to 0.98, more preferably from 0.24 to 0.8, and still more preferably from 0.32 to 0.67.

When the component (D1) is titanium, the value of b in formula (I) is preferably from 0.0006 to 0.67, more preferably from 0.033 to 0.57, and still more preferably from 0.089 to 0.44.

When the component (D1) is titanium, the value of c in formula (I) is preferably from 0.00056 to 0.51, more preferably from 0.026 to 0.42, and still more preferably from 0.075 to 0.33.

When the component (D1) is titanium, the value of d in formula (I) is preferably from 0.0026 to 0.94, more preferably from 0.02 to 0.48, and still more preferably from 0.039 to 0.25.

When the component (D1) is vanadium, the value of a in formula (I) is preferably from 0.06 to 0.98, more preferably from 0.23 to 0.8, and still more preferably from 0.27 to 0.69.

When the component (D1) is vanadium, the value of b in formula (I) is preferably from 0.00068 to 0.67, more preferably from 0.034 to 0.57, and still more preferably from 0.072 to 0.45.

When the component (D1) is vanadium, the value of c in formula (I) is preferably from 0.00064 to 0.51, more preferably from 0.027 to 0.42, and still more preferably from 0.063 to 0.33.

When the component (D1) is vanadium, the value of d in formula (I) is preferably from 0.0024 to 0.93, more preferably from 0.017 to 0.45, and still more preferably from 0.022 to 0.41.

When the component (D1) is chromium, the value of a in formula (I) is preferably from 0.061 to 0.98, more preferably from 0.23 to 0.8, and still more preferably from 0.28 to 0.69.

When the component (D1) is chromium, the value of b in formula (I) is preferably from 0.0007 to 0.67, more preferably from 0.035 to 0.57, and still more preferably from 0.073 to 0.45.

When the component (D1) is chromium, the value of c in formula (I) is preferably from 0.00065 to 0.51, more preferably from 0.027 to 0.42, and still more preferably from 0.063 to 0.33.

When the component (D1) is chromium, the value of d in formula (I) is preferably from 0.0024 to 0.93, more preferably from 0.017 to 0.44, and still more preferably from 0.022 to 0.4.

When the component (D) is the component (D2): one or more substances selected from among elements belonging to group 13 of the periodic table, the value of a in formula (I) is preferably from 0.053 to 0.98. If a is less than the aforementioned lower limit, then the amount of the component (A) is too small, and there is a possibility that the efficiency of the oxygenate synthesis may not be enhanced sufficiently, whereas if a exceeds the aforementioned upper limit, then the amounts of the components (B) to (D) become too small, and there is a possibility that the efficiency of the oxygenate synthesis may not be enhanced sufficiently.

When the component (D) is the component (D2): one or more substances selected from among elements belonging to group 13 of the periodic table, the value of b in formula (I) is preferably from 0.00059 to 0.67. If b is less than the aforementioned lower limit, then the amount of the component (B) is too small, and there is a possibility that the efficiency of the oxygenate synthesis may not be enhanced sufficiently, whereas if b exceeds the aforementioned upper limit, then the amounts of the component (A), the component (C) and the component (D) become too small, and there is a possibility that the efficiency of the oxygenate synthesis may not be enhanced sufficiently.

When the component (D) is the component (D2): one or more substances selected from among elements belonging to group 13 of the periodic table, the value of c in formula (I) is preferably from 0.00056 to 0.51. If c is less than the aforementioned lower limit, then the amount of the component (C) is too small, and there is a possibility that the efficiency of the oxygenate synthesis may not be enhanced sufficiently, whereas if c exceeds the aforementioned upper limit, then the amounts of the component (A), the component (B) and the component (D2) become too small, and there is a possibility that the efficiency of the oxygenate synthesis may not be enhanced sufficiently.

When the component (D) is the component (D2): one or more substances selected from among elements belonging to group 13 of the periodic table, the value of d in formula (I) is preferably from 0.0024 to 0.95. If d is less than the aforementioned lower limit, then the amount of the component (D2) is too small, and there is a possibility that the efficiency of the oxygenate synthesis may not be enhanced sufficiently, whereas if d exceeds the aforementioned upper limit, then the amounts of the components (A) to (C) become too small, and there is a possibility that the efficiency of the oxygenate synthesis may not be enhanced sufficiently.

When the component (D2) is boron, the value of a in formula (I) is preferably from 0.057 to 0.98, more preferably from 0.12 to 0.78, and still more preferably from 0.22 to 0.55.

When the component (D2) is boron, the value of b in formula (I) is preferably from 0.00065 to 0.67, more preferably from 0.015 to 0.57, and still more preferably from 0.055 to 0.39.

When the component (D2) is boron, the value of c in formula (I) is preferably from 0.00061 to 0.51, more preferably from 0.013 to 0.41, and still more preferably from 0.05 to 0.28.

When the component (D2) is boron, the value of d in formula (I) is preferably from 0.0024 to 0.94, more preferably from 0.028 to 0.8, and still more preferably from 0.13 to 0.57.

When the component (D2) is aluminum, the value of a in formula (I) is preferably from 0.053 to 0.98, more preferably from 0.19 to 0.78, and still more preferably from 0.22 to 0.68.

When the component (D2) is aluminum, the value of b in formula (I) is preferably from 0.00059 to 0.67, more preferably from 0.026 to 0.57, and still more preferably from 0.055 to 0.45.

When the component (D2) is aluminum, the value of c in formula (I) is preferably from 0.00056 to 0.51, more preferably from 0.022 to 0.41, and still more preferably from 0.05 to 0.33.

When the component (D2) is aluminum, the value of d in formula (I) is preferably from 0.0024 to 0.95, more preferably from 0.028 to 0.6, and still more preferably from 0.036 to 0.57.

When the component (D) is the component (D3): one or more substances selected from the group consisting of magnesium and lanthanoids, the value of a in formula (I) is preferably from 0.065 to 0.98. If a is less than the aforementioned lower limit, then the amount of the component (A) is too small, and there is a possibility that the efficiency of the oxygenate synthesis may not be enhanced sufficiently, whereas if a exceeds the aforementioned upper limit, then the amounts of the components (B) to (D3) become too small, and there is a possibility that the efficiency of the oxygenate synthesis may not be enhanced sufficiently.

When the component (D) is the component (D3): one or more substances selected from the group consisting of magnesium and lanthanoids, the value of b in formula (I) is preferably from 0.00075 to 0.67. If b is less than the aforementioned lower limit, then the amount of the component (B) is too small, and there is a possibility that the efficiency of the oxygenate synthesis may not be enhanced sufficiently, whereas if b exceeds the aforementioned upper limit, then the amounts of the component (A), the component (C) and the component (D3) become too small, and there is a possibility that the efficiency of the oxygenate synthesis may not be enhanced sufficiently.

When the component (D) is the component (D3): one or more substances selected from the group consisting of magnesium and lanthanoids, the value of c in formula (I) is preferably from 0.0007 to 0.51. If c is less than the aforementioned lower limit, then the amount of the component (C) is too small, and there is a possibility that the efficiency of the oxygenate synthesis may not be enhanced sufficiently, whereas if c exceeds the aforementioned upper limit, then the amounts of the component (A), the component (B) and the component (D3) become too small, and there is a possibility that the efficiency of the oxygenate synthesis may not be enhanced sufficiently.

When the component (D) is the component (D3): one or more substances selected from the group consisting of magnesium and lanthanoids, the value of d in formula (I) is preferably from 0.0024 to 0.93. If d is less than the aforementioned lower limit, then the amount of the component (D3) is too small, and there is a possibility that the efficiency of the oxygenate synthesis may not be enhanced sufficiently, whereas if d exceeds the aforementioned upper limit, then the amounts of the components (A) to (C) become too small, and there is a possibility that the efficiency of the oxygenate synthesis may not be enhanced sufficiently.

When the component (D3) is magnesium, the value of a in formula (I) is preferably from 0.18 to 0.78, and more preferably from 0.21 to 0.68.

When the component (D3) is magnesium, the value of b in formula (I) is preferably from 0.025 to 0.57, and more preferably from 0.052 to 0.45.

When the component (D3) is magnesium, the value of c in formula (I) is preferably from 0.021 to 0.41, and more preferably from 0.047 to 0.33.

When the component (D3) is magnesium, the value of d in formula (I) is preferably from 0.028 to 0.63, and more preferably from 0.036 to 0.59.

When the component (D3) is a lanthanoid, the value of a in formula (I) is preferably from 0.11 to 0.98, more preferably from 0.27 to 0.83, and particularly preferably from 0.33 to 0.71.

When the component (D3) is a lanthanoid, the value of b in formula (I) is preferably from 0.0014 to 0.67, more preferably from 0.044 to 0.58, and particularly preferably from 0.092 to 0.46.

When the component (D3) is a lanthanoid, the value of c in formula (I) is preferably from 0.0012 to 0.51, more preferably from 0.033 to 0.42, and particularly preferably from 0.078 to 0.34.

When the component (D3) is a lanthanoid, the value of d in formula (I) is preferably from 0.0024 to 0.83, more preferably from 0.0068 to 0.23, and particularly preferably from 0.0087 to 0.21.

In the catalyst of the present invention, each of the components (A) to (D) may exist independently, or the components (A) to (D) may form an alloy.

In the catalyst of the present invention, when the component (D) is the component (D1), each of the components (A) to (D1) may exist independently, or the components (A) to (D1) may form an alloy.

In the catalyst of the present invention, when the component (D) is the component (D2), each of the components (A) to (D2) may exist independently, or the components (A) to (D2) may form an alloy.

In the catalyst of the present invention, when the component (D) is the component (D3), each of the components (A) to (D3) may exist independently, or the components (A) to (D3) may form an alloy.

The catalyst of the present invention may be an aggregate of the components (A) to (D), the components (A) to (D1), the components (A) to (D2), or the components (A) to (D3), or may be a supported catalyst in which the components (A) to (D), the components (A) to (D1), the components (A) to (D2), or the components (A) to (D3) are supported on a carrier, and is preferably a supported catalyst. By forming the catalyst as a supported catalyst, the contact efficiency between the components (A) to (D), the components (A) to (D1), the components (A) to (D2), or the components (A) to (D3), and the mixed gas can be enhanced, and the oxygenate can be synthesized more efficiently.

Substances that are known as carriers for metal catalysts can be used as the carrier, and examples include silica, titania, alumina and ceria. Of these, from the viewpoints of improving the selectivity of the catalytic reaction and increasing the CO conversion rate, and because various products having differing specific surface areas and pore diameters can be procured commercially, silica is preferable.

The "selectivity" is a percentage indicating the number of moles of C converted to a specific oxygenate among the number of moles of CO consumed from the mixed gas. For example, in the formula (α) shown below, the selectivity for acetic acid, which represents the oxygenate, is 100 mol %. On the other hand, in the formula (β) shown below, the selectivity for acetic acid, which represents one oxygenate, is 50 mol %, and the selectivity for acetaldehyde, which represents another oxygenate, is also 50 mol %.

$$2H_2 + 2CO \rightarrow CH_3COOH \quad (\alpha)$$

$$5H_2 + 4CO \rightarrow CH_3COOH + CH_3CHO + H_2O \quad (\beta)$$

As the carrier, a substance having a specific surface area of 10 to 1,000 $m^2/g$ and having a pore diameter of at least 1 nm is preferable.

In addition, the carrier is preferably a substance having a narrow particle size distribution. Although there are no particular limitations on the average particle size of the carrier, a value of 0.5 to 5,000 µm is preferable.

Carriers having various different specific surface areas, pore diameters, pore volumes and particle sizes are available commercially, and by appropriate selection of the type of carrier, the catalytic activity and the product distribution and the like can be altered.

For example, if a carrier having a small pore diameter is selected, then it is thought that the particle sizes of the components (A) to (D), the components (A) to (D1), the components (A) to (D2), or the components (A) to (D3) supported on the carrier are reduced, and the diffusion rates of the reaction gas and the products formed when the raw material gas flows across the carrier and reacts tend to decrease, resulting in changes in the catalytic activity and the product distribution.

When the catalyst of the present invention is formed as a supported catalyst, the total amount of the components (A) to (D), the components (A) to (D1), the components (A) to (D2), or the components (A) to (D3) is preferably from 0.01 to 10 parts by mass, and more preferably from 0.1 to 5 parts by mass, per 100 parts by mass of the carrier. If this amount is less than the lower limit, then there is a possibility that the efficiency of the oxygenate synthesis may deteriorate, whereas if the amount exceeds the upper limit, then achieving a state in which the components (A) to (D), the components (A) to (D1), the components (A) to (D2), or the components (A) to (D3) are dispersed uniformly and thoroughly becomes more difficult, and there is a possibility that the efficiency of the oxygenate synthesis may deteriorate.

The catalyst of the present invention is produced in accordance with conventionally known methods for manufacturing noble metal catalysts. Examples of the method for manufacturing the catalyst include impregnation methods, dipping methods, ion exchange methods, coprecipitation methods and kneading methods, and among these, an impregnation method is preferable. By using an impregnation method, the components (A) to (D) are dispersed more uniformly in the obtained catalyst, and therefore the contact efficiency with the mixed gas is further improved, and the oxygenate can be synthesized more efficiently.

Examples of the raw material compounds for the components (A) to (D) used in preparing the catalyst include the types of compounds typically used in preparing noble metal catalysts, including inorganic salts such as oxides, chlorides, nitrates and carbonates, organic salts or chelate compounds such as oxalate salts, acetylacetonate salts, dimethylglyoxime salts and ethylenediamine acetate salts, carbonyl compounds, cyclopentadienyl compounds, ammine complexes, alkoxide compounds and alkyl compounds, which are used as compounds of the components (A) to (D), the components (A) to (D1), the components (A) to (D2), or the components (A) to (D3).

The impregnation method is described below. First, the raw material compounds for the components (A) to (D), the components (A) to (D1), the components (A) to (D2), or the components (A) to (D3) are dissolved in a solvent such as water, methanol, ethanol, tetrahydrofuran, dioxane, hexane, benzene or toluene, and the carrier is then dipped in the thus obtained solution (impregnating solution) to adhere the impregnating solution to the carrier. In those cases where a porous body is used as the carrier, the impregnating solution is allowed to penetrate thoroughly into the pores, and the solvent is then evaporated to obtain the catalyst.

Examples of methods of impregnating the carrier with an impregnating solution include a method in which the carrier is impregnated with a solution in which all of the raw material compounds have been dissolved (simultaneous method), and a method in which each raw material compound is dissolved individually to prepare a series of solutions, and the carrier is then impregnated sequentially with each solution (sequential method). Of these, the sequential method is preferable. A catalyst obtained using the sequential method enables more efficient synthesis of the oxygenate.

Examples of the sequential method include a method in which the carrier is impregnated with a solution (primary impregnating solution) containing the component (D), the component (D1), the component (D2) or the component (D3) (primary impregnation step), the carrier is then dried to obtain a primary support body on which the component (D), the component (D1), the component (D2) or the component (D3) has been supported (primary support step), the primary support body is subsequently impregnated with a solution (secondary impregnating solution) containing the components (A) to (C) (secondary impregnation step), and the support body is then dried (secondary support step). In this manner, by first supporting the component (D), the component (D1), the component (D2) or the component (D3) on the carrier, and subsequently supporting the components (A) to (C) on the carrier, a catalyst is obtained in which the components (A) to (D), the components (A) to (D1), the components (A) to (D2), or the components (A) to (D3) are more highly dispersed, thus enabling more efficient synthesis of the oxygenate.

The primary support step uses a method in which, for example, the carrier impregnated with the primary impregnating solution is dried (primary drying operation), and the carrier is then heated and baked at an arbitrary temperature (primary baking step). There are no particular limitations on the drying method used in the primary drying operation, and examples include a method in which the carrier impregnated with the primary impregnating solution is heated at an arbitrary temperature. The heating temperature used in the primary drying operation may be any temperature capable of evaporating the solvent of the primary impregnating solution, and when the solvent is water, is typically within a range from 80 to 120° C. The heating temperature in the primary baking operation is, for example, within a range from 300 to 600° C. By performing the primary baking operation, those components contained within the raw material compounds for the component (D), the component (D1), the component (D2) or the component (D3) that do not contribute to the catalytic reaction can be satisfactorily volatilized, thereby further enhancing the catalytic activity.

The secondary support step uses a method in which, for example, the primary support body impregnated with the secondary impregnating solution is dried (secondary drying operation), and the support body is then heated and baked at an arbitrary temperature (secondary baking step).

There are no particular limitations on the drying method used in the secondary drying operation, and examples include a method in which the primary support body impregnated with the secondary impregnating solution is heated at an arbitrary temperature. The heating temperature used in the secondary drying operation may be any temperature capable of evaporating the solvent of the secondary impregnating solution, and when the solvent is water, is typically within a range from 80 to 120° C. The heating temperature in the secondary baking operation is, for example, within a range from 300 to 600° C. By performing the secondary baking operation, those components contained within the raw material compounds for the components (A) to (C) that do not contribute to the catalytic reaction can be satisfactorily volatilized, thereby further enhancing the catalytic activity.

The catalyst prepared using the method described above is usually subjected to a reduction treatment to activate the catalyst, and is then used in oxygenate synthesis. For the reduction treatment, a method in which the catalyst is brought into contact with a gas containing hydrogen is simple and preferable. In this case, the treatment temperature may be any temperature above the temperature at which rhodium is reduced, namely a temperature of approximately 100° C., but is preferably within a range from 200 to 600° C. In addition, for the purpose of achieving satisfactory dispersion of the components (A) to (D), the components (A) to (D1), the components (A) to (D2), or the components (A) to (D3), the hydrogen reduction may be performed while the temperature is increased from a low temperature in a gradual or stepwise manner. Further, the catalyst may also be subjected to a reduction treatment in the presence of carbon monoxide and water, or in the presence of a reducing agent such as hydrazine, a boron hydride compound, or an aluminum hydride compound.

The heating time during the reduction treatment is, for example, preferably from 1 to 10 hours, and more preferably from 2 to 5 hours. If the time is less than the aforementioned lower limit, then there is a possibility that the reduction of the components (A) to (D), the components (A) to (D1), the components (A) to (D2), or the components (A) to (D3) may be inadequate, causing a deterioration in the production efficiency for the oxygenate. If the time exceeds the upper limit, then there is a possibility that the metal particles in the components (A) to (D), the components (A) to (D1), the components (A) to (D2), or the components (A) to (D3) may aggregate, causing a deterioration in the efficiency of the oxygenate synthesis, and the energy required for the reduction treatment becomes excessive, which is economically disadvantageous.

A surface treatment step of bringing the primary support body into contact with an alkaline aqueous solution to effect a surface treatment may be provided after the primary support step but prior to the secondary impregnation step. By providing a surface treatment step, a portion of the surface of the primary support body is converted to hydroxides, which is thought to further improve the dispersibility of the metal particles contained in the component (A).

The alkaline aqueous solution used in the surface treatment step can be selected with due consideration of the type of the component (D), the component (D1), the component (D2) or the component (D3), and the type of the carrier and the like, and for example, an aqueous solution of ammonia or the like may be used. The concentration of the alkaline aqueous solution can be determined with due consideration of the type of the component (D), the component (D1), the component (D2) or the component (D3), but for example, is typically from 0.1 to 3 mol/L.

There are no particular limitations on the method used for bringing the alkaline aqueous solution into contact with the primary support body (the contact method), and examples include a method in which the primary support body is dipped in the alkaline aqueous solution, and a method in which the alkaline aqueous solution is applied to the primary support body by spraying or the like.

The time for which the alkaline aqueous solution is brought into contact with the primary support body (the contact time) may be determined with due consideration of the contact method and the concentration of the alkaline aqueous solution and the like, but for example, in those cases where the primary support body is dipped in the alkaline aqueous solution, a time of 0.1 to 12 hours is preferable, and a time of 1 to 8 hours is more preferable. If the time is less than the aforementioned lower limit, then it is difficult to achieve the effects provided by this step, whereas even if the time exceeds the upper limit, there is a possibility that no further improvement in the catalytic activity is obtainable.

There are no particular limitations on the temperature of the alkaline aqueous solution during the surface treatment step, but for example, the temperature is preferably from 5 to 40° C., and more preferably from 15 to 30° C. If the temperature is less than the aforementioned lower limit, then the contact time becomes too long, and there is a possibility that the productivity of the catalyst may deteriorate, whereas if the temperature exceeds the upper limit, then there is a concern that the component (D) supported on the primary support body may melt or degenerate.

(Device for Manufacturing Oxygenate)

A device for manufacturing an oxygenate according to the present invention (hereafter also referred to as simply "the manufacturing device") includes a reaction tube packed with the catalyst of the present invention, a supply unit for supplying the mixed gas into the reaction tube, and a discharge unit for discharging the product from the reaction tube.

One example of the manufacturing device of the present invention is described using FIG. 1. FIG. 1 is a schematic view illustrating a manufacturing device 10 according to an embodiment of the present invention. The manufacturing device 10 includes a reaction tube 1 which is packed with the catalyst to form a reaction bed 2, a supply tube 3 which is connected to the reaction tube 1, a discharge tube 4 which is connected to the reaction tube 1, a temperature control unit 5 which is connected to the reaction tube 1, and a pressure control unit 6 which is provided in the discharge tube 4.

The reaction tube 1 is preferably formed from a material that is inert relative to the raw material gas and the synthesized oxygenate, and preferably has a shape that is resistant to heating of approximately 100 to 500° C. or pressure of approximately 10 MPa.

An example of the reaction tube 1 is a substantially circular cylindrical member formed from stainless steel.

The supply tube 3 is a supply unit for supplying the mixed gas into the reaction tube 1, and for example, is a pipe formed from stainless steel or the like.

The discharge tube 4 is a discharge unit for discharging the synthesized gas (product) containing the oxygenate synthesized in the reaction bed 2, and for example, is a pipe formed from stainless steel or the like.

The temperature control unit 5 may be any device capable of adjusting the reaction bed 2 inside the reaction tube 1 to an arbitrary temperature, and examples include an electric furnace or the like.

The pressure control unit 6 may be any device capable of adjusting the pressure inside the reaction tube 1 to an arbitrary pressure, and for example, a conventional pressure valve or the like may be used.

Further, the manufacturing device 10 may also include other conventional equipment such as a mass flow or a gas flow rate control unit for adjusting the flow rate of the gas.

(Method for Manufacturing Oxygenate)

A method for manufacturing an oxygenate according to the present invention is a method for bringing the mixed gas into contact with the catalyst. One example of the method for manufacturing an oxygenate according to the present invention is described below using the manufacturing device illustrated in FIG. 1.

First, the inside of the reaction tube 1 is set to an arbitrary temperature and an arbitrary pressure, and a mixed gas 20 is then introduced from the supply tube 3 into the reaction tube 1.

There are no particular limitations on the mixed gas 20, provided it contains hydrogen and carbon monoxide, and for example, a mixed gas prepared from natural gas or coal may be used, or a biomass gas obtained by gasifying a biomass may be used. Biomass gases can be obtained by conventionally known methods, for example by heating a pulverized biomass in the presence of steam (for example, at a temperature of 800 to 1,000° C.).

In those cases where a biomass gas is used as the mixed gas 20, the mixed gas 20 may be subjected to a gas purification treatment, for the purpose of removing impurities such as the tar fraction, sulfur fraction, nitrogen fraction, chlorine fraction and moisture fraction, prior to being supplied to the reaction tube 1. Examples of methods that may be employed as the gas purification treatment include any of the methods known within the technical field, including wet methods and dry methods. Examples of the wet methods include the sodium hydroxide method, ammonia absorption method, lime-gypsum method and magnesium hydroxide method, whereas examples of the dry methods include activated carbon adsorption methods such as the pressure swing adsorption (PSA) method, and an electron beam method.

The mixed gas 20 is preferably a gas containing hydrogen and carbon monoxide as the main components, namely a gas in which the total amount of hydrogen and carbon monoxide within the mixed gas 20 is preferably at least 50% by volume, more preferably at least 80% by volume, still more preferably 90% by volume or more, and may be 100% by volume. The larger the hydrogen and carbon monoxide content, the greater the amount of oxygenate produced, meaning the oxygenate can be manufactured more efficiently.

The volumetric ratio represented by hydrogen/carbon monoxide (hereafter also referred to as the $H_2/CO$ ratio) is preferably within a range from 0.1 to 10, more preferably from 0.5 to 3, and still more preferably from 1.5 to 2.5. When the ratio satisfies this range, it is stoichiometrically appropriate for the reaction that generates the oxygenate from the mixed gas, meaning the oxygenate can be manufactured more efficiently.

Besides the hydrogen and carbon monoxide, the mixed gas 20 may also contain methane, ethane, ethylene, nitrogen, carbon dioxide, or water or the like.

The temperature when the mixed gas 20 and the catalyst are brought into contact (the reaction temperature), namely the temperature inside the reaction tube 1, is preferably within a range from 150 to 450° C., more preferably from 200 to 400° C., and still more preferably from 250 to 350° C. When the temperature is at least as large as the aforementioned lower limit, the rate of the catalytic reaction can be increased satisfactorily, and the oxygenate can be manufactured more efficiently. When the temperature is not more than the upper limit, the oxygenate synthesis reaction becomes the main reaction, and the oxygenate can be manufactured more efficiently.

Further, the catalytic activity and the product distribution and the like can be adjusted by altering the reaction temperature. With the catalyst of the present invention, the higher the reaction temperature, the higher the selectivity for hydrocarbons such as methane, and the lower the total of the selectivity for ethanol and the selectivity for aldehydes, but the CO conversion rate and the ethanol selectivity tend to improve, meaning the amount of ethanol produced can be increased. The lower the reaction temperature, the lower the CO conversion rate becomes, but the total of the selectivity for ethanol and the selectivity for aldehydes tends to increase, and the selectivity for acetaldehyde is particularly enhanced, meaning the amount of acetaldehyde produced can be increased.

Accordingly, by selecting an appropriate reaction temperature according to need, the amount of ethanol or acetaldehyde produced can be adjusted.

For example, at a reaction temperature of 300° C. or higher, and particularly at a reaction temperature of 300 to 320° C., the selectivity for ethanol tends to be enhanced, whereas at a reaction temperature of less than 300° C., and particularly at a reaction temperature of 260 to 280° C., the selectivity for acetaldehyde tends to be enhanced.

The pressure when the mixed gas 20 and the catalyst are brought into contact (the reaction pressure), namely the pressure inside the reaction tube 1, is preferably within a range from 0.5 to 10 MPa, more preferably from 1 to 7.5 MPa, and still more preferably from 2 to 5 MPa. When the pressure is at least as large as the aforementioned lower limit, the rate of the catalytic reaction can be increased satisfactorily, and the oxygenate can be manufactured more efficiently. When the pressure is not more than the upper limit, the oxygenate synthesis reaction becomes the main reaction, and the oxygenate can be manufactured more efficiently.

The introduced mixed gas 20 flows through the reaction tube while making contact with the catalyst in the reaction bed 2, and a portion of the mixed gas is converted to oxygenates.

While flowing through the reaction bed 2, the mixed gas 20 generates oxygenate compounds, for example by the catalytic reactions represented by formulas (1) to (5) shown below.

$$3H_2 + 2CO \rightarrow CH_3CHO + H_2O \quad (1)$$

$$4H_2 + 2CO \rightarrow CH_3CH_2OH + H_2O \quad (2)$$

$$H_2 + CH_3CHO \rightarrow CH_3CH_2OH \quad (3)$$

$$2H_2 + 2CO \rightarrow CH_3COOH \quad (4)$$

$$2H_2 + CH_3COOH \rightarrow CH_3CH_2OH + H_2O \quad (5)$$

A synthesis gas 22 containing these oxygenates is discharged from the discharge tube 4. There are no particular limitations on the synthesis gas 22 provided it contains the oxygenate, but a gas containing at least one compound selected from among acetic acid, ethanol and acetaldehyde is preferable, and a gas containing ethanol is more preferable. This is because the effects of the catalyst of the present invention are particularly dramatic in methods of manufacturing this type of C2 compound.

The supply rate of the mixed gas 20 is preferably adjusted so that, for example, the space velocity of the mixed gas in the reaction bed 2 (the value obtained by dividing the gas supply volume per unit of time by the amount of the catalyst (converted to volume)), calculated as a standard state value, is within a range from 10 to 100,000 L/L-catalyst/h.

The space velocity is adjusted as appropriate, with due consideration of the reaction pressure and reaction temperature appropriate for the targeted oxygenate, and the composition of the mixed gas that represents the raw material.

If necessary, the synthesis gas 22 discharged from the discharge tube 4 may be processed in a gas-liquid separator or the like to separate the unreacted mixed gas 20 and the oxygenate.

In the present embodiment, the mixed gas is brought into contact with the fixed bed of the reaction bed 2, but the catalyst may also be formed in a configuration other than a fixed bed, such as a fluidized bed or a moving bed, and the mixed gas then brought into contact with this bed.

In the present invention, the obtained oxygenate may, if necessary, be separated into the required components using distillation or the like.

Further, in the present invention, a step of hydrogenating products other than ethanol (for example, C2 compounds excluding ethanol, such as acetic acid and acetaldehyde, and esters such as ethyl acetate, methyl acetate and ethyl formate) and converting these products to ethanol (an ethanolization step) may also be provided. An example of the ethanolization step is a method in which oxygenates including acetaldehyde and acetic acid and the like are brought into contact with a hydrogenation catalyst to effect a conversion to ethanol.

The types of catalysts known in this technical field can be used as the hydrogenation catalyst, and examples include copper, copper-zinc, copper-chromium, copper-zinc-chromium, iron, rhodium-iron, rhodium-molybdenum, palladium, palladium-iron, palladium-molybdenum, iridium-iron, rhodium-iridium-iron, iridium-molybdenum, rhenium-zinc, platinum, nickel, cobalt, ruthenium, rhodium oxide, palladium oxide, platinum oxide and ruthenium oxide. These hydrogenation catalysts may be supported catalysts in which the catalyst is supported on the same type of carrier as that used in the catalyst of the present invention, and supported catalysts in which copper, copper-zinc, copper-chromium or copper-zinc-chromium are supported on a silica-based carrier are ideal. Examples of the method for manufacturing the supported hydrogenation catalyst include the same simultaneous and sequential methods as those described for the catalyst of the present invention.

Alternatively, in order to obtain acetaldehyde with good efficiency in the present invention, the product may be processed with a gas-liquid separator or the like to extract the ethanol, and a step then provided to convert this ethanol to acetaldehyde by performing an oxidation.

Examples of methods of oxidizing the ethanol include a method in which the ethanol is liquefied or gasified, and subsequently brought into contact with an oxidation catalyst such as a metal catalyst containing gold, platinum, ruthenium, copper or manganese as the main component, or an alloy catalyst containing 2 or more of these metals. These oxidation catalysts may be supported catalysts in which the metal is supported on the same type of carrier as that used in the catalyst of the present invention.

As described above, by using the catalyst of the present invention, an oxygenate can be synthesized efficiently from the mixed gas.

In addition, by using the catalyst of the present invention, the amount of ethanol within the oxygenate product can be increased.

EXAMPLES

The present invention is described below using a series of examples, but the present invention is in no way limited by these examples.

Examples A1, 10 to 12

First, 1.08 mL of an aqueous solution containing 0.0307 g of an ammonium titanium lactate salt (Ti(OH)$_2$[OCH(CH$_3$)

COO⁻]₂(NH₄⁺)₂) (the primary impregnating solution) was added dropwise to 1.0 g of a silica gel (specific surface area: 310 m²/g, average pore diameter: 14 nm, pore volume: 1.1 cm³/g) to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.061 g of rhodium chloride (RhCl₃), 0.0017 g of lithium chloride (LiCl) and 0.0159 g of manganese chloride tetrahydrate (MnCl₂.4H₂O) (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/SiO₂, and Rh:Mn:Li:Ti=0.565:0.155:0.078:0.202 (molar ratio). In Tables A1 and A2, the method for manufacturing the catalysts in these examples is recorded as the "sequential method".

Example A2

With the exception of using 1.08 mL of an aqueous solution containing 0.061 g of rhodium chloride, 0.0062 g of lithium chloride and 0.0288 g of manganese chloride tetrahydrate as the secondary impregnating solution, a catalyst was obtained in the same manner as Example A1.

The thus obtained catalyst had a rhodium support ratio of 3 mass %/SiO₂, and Rh:Mn:Li:Ti=0.424:0.212:0.212:0.152 (molar ratio). In Table A1, the method for manufacturing the catalyst in this example is recorded as the "sequential method".

Example A3

First, 1.08 mL of an aqueous solution containing 0.0307 g of the ammonium titanium lactate salt, 0.061 g of rhodium chloride, 0.0062 g of lithium chloride and 0.0288 g of manganese chloride tetrahydrate was added dropwise to the silica gel to impregnate the silica gel. The resulting mixture was dried at 110° C. for 3 hours, and then baked at 450° C. for 3 hours to obtain a catalyst.

The thus obtained catalyst had a rhodium support ratio of 3 mass %/SiO₂, and Rh:Mn:Li:Ti=0.424:0.212:0.212:0.152 (molar ratio). In Table A1, the method for manufacturing the catalyst in this example is recorded as the "simultaneous method".

Example A4

With the exceptions of using 1.08 mL of an aqueous solution containing 0.0123 g of the ammonium titanium lactate salt as the primary impregnating solution, and using 1.08 mL of an aqueous solution containing 0.061 g of rhodium chloride, 0.0062 g of lithium chloride and 0.0432 g of manganese chloride tetrahydrate as the secondary impregnating solution, a catalyst was obtained in the same manner as Example A1.

The thus obtained catalyst had a rhodium support ratio of 3 mass %/SiO₂, and Rh:Mn:Li:Ti=0.417:0.313:0.208:0.062 (molar ratio). In Table A1, the method for manufacturing the catalyst in this example is recorded as the "sequential method".

Example A5

With the exception of using 1.08 mL of an aqueous solution containing 0.0920 g of the ammonium titanium lactate salt as the primary impregnating solution, a catalyst was obtained in the same manner as Example A2.

The thus obtained catalyst had a rhodium support ratio of 3 mass %/SiO₂, and Rh:Mn:Li:Ti=0.325:0.162:0.162:0.351 (molar ratio). In Table A1, the method for manufacturing the catalyst in this example is recorded as the "sequential method".

Example A6

First, 1.08 mL of an aqueous solution containing 0.0115 g of ammonium metavanadate (H₄NO₃V) (the primary impregnating solution) was added dropwise to 1.0 g of the silica gel to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.0300 g of rhodium chloride, 0.00028 g of lithium chloride and 0.0044 g of manganese chloride tetrahydrate (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/SiO₂, and Rh:Mn:Li:V=0.581:0.160:0.080:0.179 (molar ratio). In Table A1, the method for manufacturing the catalyst in this example is recorded as the "sequential method".

Example A7

First, 1.08 mL of an aqueous solution containing 0.0385 g of chromium nitrate nonahydrate (Cr(NO₃)₃.9H₂O) (the primary impregnating solution) was added dropwise to 1.0 g of the silica gel to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.0300 g of rhodium chloride, 0.00028 g of lithium chloride and 0.0044 g of manganese chloride tetrahydrate (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/SiO₂, and Rh:Mn:Li:Cr=0.583:0.160:0.080:0.177 (molar ratio). In Table A1, the method for manufacturing the catalyst in this example is recorded as the "sequential method".

Example A8

With the exception of dipping the primary support body in a 2 mol/L aqueous solution of ammonia for 6 hours, and subsequently drying the support body at 110° C. for 2 hours before supplying it to the secondary impregnation step, a catalyst was obtained in the same manner as Example A2.

The thus obtained catalyst had a rhodium support ratio of 3 mass %/SiO$_2$, and Rh:Mn:Li:Ti=0.424:0.212:0.212:0.152 (molar ratio). In Table A1, the method for manufacturing the catalyst in this example is recorded as the "hydroxide method".

Example A9

With the exception of dipping the primary support body in a 2 mol/L aqueous solution of ammonia for 6 hours, and subsequently drying the support body at 110° C. for 2 hours before supplying it to the secondary impregnation step, a catalyst was obtained in the same manner as Example A5.

The thus obtained catalyst had a rhodium support ratio of 3 mass %/SiO$_2$, and Rh:Mn:Li:Ti=0.325:0.162:0.162:0.351 (molar ratio). In Table A1, the method for manufacturing the catalyst in this example is recorded as the "hydroxide method".

Comparative Examples A1, A3 to A5

First, 1.08 mL of an aqueous solution containing 0.061 g of rhodium chloride, 0.0017 g of lithium chloride and 0.0159 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst.

The thus obtained catalyst had a rhodium support ratio of 3 mass %/SiO$_2$, and Rh:Mn:Li=0.708:0.194:0.098 (molar ratio). In Table A2, the method for manufacturing the catalysts in these examples is recorded as the "simultaneous method".

Comparative Example A2

First, 1.08 mL of an aqueous solution containing 0.061 g of rhodium chloride, 0.0062 g of lithium chloride and 0.0288 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst. The thus obtained catalyst had a rhodium support ratio of 3 mass %/SiO$_2$, and Rh:Mn:Li=0.500:0.250:0.250 (molar ratio). In Table A2, the method for manufacturing the catalyst in this example is recorded as the "simultaneous method".

(Evaluation Method)

A 0.1 g sample of the catalyst from each example was packed in a circular cylindrical reaction tube formed from stainless steel having a diameter of 2 mm and a length of 15 cm, thus forming a reaction bed. The reaction bed was heated at 320° C. for 2.5 hours while hydrogen was passed through the reaction bed at normal pressure at a space velocity of 1200 L/L-catalyst/h, thereby subjecting the catalyst to a reduction treatment.

Subsequently, under conditions including the reaction temperature shown in Table A1 or A2 and a reaction pressure of 2 MPa, a mixed gas (H$_2$/CO ratio=2) was passed through the reaction bed at a space velocity shown in Table A1 or A2, and a synthesis gas containing oxygenates was manufactured.

The mixed gas was passed through the reaction bed for 3 hours, and the obtained synthesis gas was collected and analyzed by gas chromatography.

From the thus obtained data, the CO conversion rate (mol %), the ethanol and acetaldehyde selectivity values (mol %), and the amounts produced of ethanol and acetaldehyde (g/L-catalyst/h) were calculated. These results are shown in Tables A1 and A2. The amounts produced of ethanol and acetaldehyde are values that indicate the mass of product per unit volume of catalyst per unit of time.

TABLE A1

| | | Example | | | | | | | | |
|---|---|---|---|---|---|---|---|---|---|---|
| | | 1 | 2 | 3 | 4 | 5 | 6 | 7 | 8 | 9 |
| Composition (molar ratio) | Rhodium | 0.565 | 0.424 | 0.424 | 0.417 | 0.325 | 0.581 | 0.583 | 0.424 | 0.325 |
| | Manganese | 0.155 | 0.212 | 0.212 | 0.313 | 0.162 | 0.160 | 0.160 | 0.212 | 0.162 |
| | Lithium | 0.078 | 0.212 | 0.212 | 0.212 | 0.208 | 0.162 | 0.080 | 0.080 | 0.212 | 0.162 |
| | Titanium | 0.202 | 0.152 | 0.152 | 0.062 | 0.351 | — | — | 0.152 | 0.351 |
| | Vanadium | — | — | — | — | — | 0.179 | — | — | — |
| | Chromium | — | — | — | — | — | — | 0.177 | — | — |
| Manufacturing method | | sequential method | sequential method | simultaneous method | sequential method | sequential method | sequential method | sequential method | hydroxide method | hydroxide method |
| Reaction temperature (° C.) | | 300 | 300 | 300 | 300 | 300 | 300 | 300 | 300 | 300 |
| Mixed gas space velocity (L/L-catalyst/h) | | 6300 | 8400 | 8400 | 8400 | 8400 | 6300 | 6300 | 8400 | 8400 |
| CO conversion rate (mol %) | | 37.7 | 26.3 | 27.7 | 39.4 | 21.0 | 23.5 | 15.2 | 50.4 | 34.1 |
| Selectivity (mol %) | Acetaldehyde | 25.6 | 47.0 | 53.0 | 48.0 | 31.7 | 29.3 | 35.0 | 20.5 | 27.1 |
| | Ethanol | 40.7 | 25.2 | 15.4 | 16.5 | 40.4 | 30.1 | 34.3 | 24.9 | 22.7 |
| | Total | 66.3 | 72.1 | 68.4 | 64.6 | 72.0 | 59.5 | 69.3 | 45.4 | 49.8 |
| Amount produced (g/L-catalyst/h) | Acetaldehyde | 198 | 338 | 383 | 517 | 174 | 141 | 109 | 270 | 242 |
| | Ethanol | 315 | 181 | 111 | 178 | 221 | 145 | 106 | 343 | 212 |
| | Total | 513 | 519 | 495 | 695 | 395 | 287 | 215 | 613 | 454 |

TABLE A2

| | | Example | | | Comparative Example | | | | |
|---|---|---|---|---|---|---|---|---|---|
| | | 10 | 11 | 12 | 1 | 2 | 3 | 4 | 5 |
| Composition (molar ratio) | Rhodium | 0.565 | 0.565 | 0.565 | 0.708 | 0.500 | 0.708 | 0.708 | 0.708 |
| | Manganese | 0.155 | 0.155 | 0.155 | 0.194 | 0.250 | 0.194 | 0.194 | 0.194 |

TABLE A2-continued

|  |  | Example | | | Comparative Example | | | | |
| --- | --- | --- | --- | --- | --- | --- | --- | --- | --- |
|  |  | 10 | 11 | 12 | 1 | 2 | 3 | 4 | 5 |
|  | Lithium | 0.078 | 0.078 | 0.078 | 0.098 | 0.250 | 0.098 | 0.098 | 0.098 |
|  | Titanium | 0.202 | 0.202 | 0.202 | — | — | — | — | — |
|  | Vanadium | — | — | — | — | — | — | — | — |
|  | Chromium | — | — | — | — | — | — | — | — |
| Manufacturing method |  | sequential method | sequential method | sequential method | simultaneous method | simultaneous method | simultaneous method | simultaneous method | simultaneous method |
| Reaction temperature (° C.) |  | 260 | 280 | 320 | 300 | 300 | 260 | 280 | 320 |
| Mixed gas space velocity (L/L-catalyst/h) |  | 6300 | 6300 | 6300 | 6300 | 8400 | 6300 | 6300 | 6300 |
| CO conversion rate (mol %) |  | 15.7 | 26.2 | 48.3 | 12.3 | 17.1 | 3.2 | 6.8 | 22.3 |
| Selectivity (mol %) | Acetaldehyde | 67.1 | 49.2 | 10.2 | 47.0 | 48.5 | 71.8 | 62.2 | 27.4 |
|  | Ethanol | 17.1 | 30.1 | 31.3 | 23.2 | 13.4 | 8.5 | 13.8 | 29.7 |
|  | Total | 84.2 | 79.3 | 41.4 | 70.2 | 61.9 | 80.3 | 76.0 | 57.0 |
| Amount produced (g/L-catalyst/h) | Acetaldehyde | 207 | 253 | 96 | 119 | 217 | 44 | 83 | 120 |
|  | Ethanol | 55 | 162 | 310 | 58 | 60 | 6 | 19 | 136 |
|  | Total | 262 | 414 | 406 | 177 | 277 | 50 | 102 | 256 |

As illustrated in Tables A1 and A2, Examples A1 to A9 applicable to the present invention exhibited a CO conversion rate of 15.2 mol % or greater, and yielded a total amount of produced oxygenates (total of acetaldehyde and ethanol) of 215 g/L-catalyst/h or greater. In addition, in Examples A1 to A9, the amount of ethanol produced was 106 g/L-catalyst/h or greater.

Comparison of Examples A1 and A10 to A12 and Comparative Examples A1 and A3 to A5 reveals that, at any reaction temperature, the total amount of oxygenates produced in the example was higher than the total amount of oxygenates produced in the corresponding comparative example.

Comparison of Examples A1 and A6 to A7 and Comparative Example A1, in which the space velocity of the mixed gas was 6300 L/L-catalyst/h, reveals that, compared with Comparative Example A1, the total amount of oxygenates produced and the amount of ethanol produced was higher in Examples A1 and A6 to A7.

Further, comparison of Examples A2 to A5 and Comparative Example A2, in which the space velocity of the mixed gas was 8400 L/L-catalyst/h, reveals that, compared with Comparative Example A2, the total amount of oxygenates produced and the amount of ethanol produced was higher in Examples A2 to A5.

Based on these results it was evident that by applying the present invention, the total amount of oxygenates produced could be increased, meaning the oxygenates could be synthesized efficiently from the mixed gas.

In addition, comparison of Example A2 and Example A3 reveals that, compared with Example 3 in which manufacturing was performed using the simultaneous method, Example A2 in which manufacturing was performed using the sequential method yielded a marked increase in the amount of ethanol produced.

Moreover, comparison of Example A2 and Example A8, and comparison of Example A5 and Example A9 reveals that, compared with Examples A2 and A5 in which manufacturing was performed using the sequential method, Examples A8 and A9 in which manufacturing was performed using the hydroxide method yielded an increase in the total amount of oxygenates produced.

The ethanol selectivity in Examples A1 and A12, in which the reaction temperature was set to 300 to 320° C., was 31.3 mol % or greater, which was higher than the ethanol selectivity in Examples A10 and A11, in which the reaction temperature was set to 260 to 280° C.

On the other hand, the acetaldehyde selectivity in Examples A10 and A11, in which the reaction temperature was set to 260 to 280° C., was 49.2 mol % or greater, which was higher than the acetaldehyde selectivity in Examples A1 and A12, in which the reaction temperature was set to 300 to 320° C.

Based on these results it was evident that by changing the reaction temperature, the selectivity for ethanol or acetaldehyde could be increased.

Examples B1, B6 to B8

First, 1.08 mL of an aqueous solution containing 0.0252 g of ammonium pentaborate octahydrate $((NH_4)_2O.B_{10}O_{16}.8H_2O)$ (the primary impregnating solution) was added dropwise to 1.0 g of a silica gel (specific surface area: 310 m$^2$/g, average pore diameter: 14 nm, pore volume: 1.1 cm$^3$/g) to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.061 g of rhodium chloride ($RhCl_3$), 0.0017 g of lithium chloride (LiCl) and 0.0159 g of manganese chloride tetrahydrate ($MnCl_2.4H_2O$) (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/$SiO_2$, and Rh:Mn:Li:B=0.348:0.096:0.048:0.508 (molar ratio). In Table B1, the method for manufacturing the catalysts in these examples is recorded as the "sequential method".

Example B2

With the exception of using 1.08 mL of an aqueous solution containing 0.061 g of rhodium chloride, 0.0062 g of lithium chloride and 0.0288 g of manganese chloride tetrahydrate as the secondary impregnating solution, a catalyst was obtained in the same manner as Example B1. The thus obtained catalyst had a rhodium support ratio of 3 mass %/SiO$_2$, and Rh:Mn:Li:B=0.289:0.145:0.145:0.421 (molar ratio). In Table B1, the method for manufacturing the catalyst in this example is recorded as the "sequential method".

Example B3

First, 1.08 mL of an aqueous solution containing 0.0252 g of ammonium pentaborate octahydrate, 0.061 g of rhodium chloride, 0.0062 g of lithium chloride and 0.0288 g of manganese chloride tetrahydrate was added dropwise to the silica gel to impregnate the silica gel. The resulting mixture was dried at 110° C. for 3 hours, and then baked at 450° C. for 3 hours to obtain a catalyst. The thus obtained catalyst had a rhodium support ratio of 3 mass %/SiO$_2$, and Rh:Mn:Li:B=0.289:0.145:0.145:0.421 (molar ratio). In Table B1, the method for manufacturing the catalyst in this example is recorded as the "simultaneous method".

Example B4

With the exceptions of using 1.08 mL of an aqueous solution containing 0.0101 g of ammonium pentaborate octahydrate as the primary impregnating solution, and using 1.08 mL of an aqueous solution containing 0.061 g of rhodium chloride, 0.0062 g of lithium chloride and 0.0432 g of manganese chloride tetrahydrate as the secondary impregnating solution, a catalyst was obtained in the same manner as Example B1.

The thus obtained catalyst had a rhodium support ratio of 3 mass %/SiO$_2$, and Rh:Mn:Li:B=0.352:0.264:0.176:0.208 (molar ratio). In Table B1, the method for manufacturing the catalyst in this example is recorded as the "sequential method".

Example B5

First, 1.08 mL of an aqueous solution containing 0.0695 g of aluminum nitrate nonahydrate (Al(NO$_3$)$_3$.9H$_2$O) (the primary impregnating solution) was added dropwise to 1.0 g of the silica gel to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.061 g of rhodium chloride, 0.0017 g of lithium chloride and 0.0159 g of manganese chloride tetrahydrate (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/SiO$_2$, and Rh:Mn:Li:Al=0.501:0.138:0.069:0.292 (molar ratio). In Table B1, the method for manufacturing the catalyst in this example is recorded as the "sequential method".

Comparative Examples B1, B3 to B5

First, 1.08 mL of an aqueous solution containing 0.061 g of rhodium chloride, 0.0017 g of lithium chloride and 0.0159 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst.

The thus obtained catalyst had a rhodium support ratio of 3 mass %/SiO$_2$, and Rh:Mn:Li=0.708:0.194:0.098 (molar ratio). In Table B2, the method for manufacturing the catalysts in these examples is recorded as the "simultaneous method".

Comparative Example B2

First, 1.08 mL of an aqueous solution containing 0.061 g of rhodium chloride, 0.0062 g of lithium chloride and 0.0288 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst.

The thus obtained catalyst had a rhodium support ratio of 3 mass %/SiO$_2$, and Rh:Mn:Li=0.500:0.250:0.250 (molar ratio). In Table B2, the method for manufacturing the catalyst in this example is recorded as the "simultaneous method".

(Evaluation Method)

A 0.1 g sample of the catalyst from each example was packed in a circular cylindrical reaction tube formed from stainless steel having a diameter of 2 mm and a length of 15 cm, thus forming a reaction bed. The reaction bed was heated at 320° C. for 2.5 hours while hydrogen was passed through the reaction bed at normal pressure at a space velocity of 1200 L/L-catalyst/h, thereby subjecting the catalyst to a reduction treatment.

Subsequently, under conditions including the reaction temperature shown in Table B1 or B2 and a reaction pressure of 2 MPa, a mixed gas (H$_2$/CO ratio=2) was passed through the reaction bed at a space velocity shown in Table B1 or B2, and a synthesis gas containing oxygenates was manufactured.

The mixed gas was passed through the reaction bed for 3 hours, and the obtained synthesis gas was collected and analyzed by gas chromatography.

From the thus obtained data, the CO conversion rate (mol %), the ethanol and acetaldehyde selectivity values (mol %), and the amounts produced of ethanol and acetaldehyde (g/L-catalyst/h) were calculated. These results are shown in Tables B1 and B2. The amounts produced of ethanol and acetaldehyde are values that indicate the mass of product per unit volume of catalyst per unit of time.

TABLE B1

| | | Example | | | | | | | |
| --- | --- | --- | --- | --- | --- | --- | --- | --- | --- |
| | | 1 | 2 | 3 | 4 | 5 | 6 | 7 | 8 |
| Composition (molar ratio) | Rhodium | 0.348 | 0.289 | 0.289 | 0.352 | 0.501 | 0.348 | 0.348 | 0.348 |
| | Manganese | 0.096 | 0.145 | 0.145 | 0.264 | 0.138 | 0.096 | 0.096 | 0.096 |
| | Lithium | 0.048 | 0.145 | 0.145 | 0.176 | 0.069 | 0.048 | 0.048 | 0.048 |

TABLE B1-continued

| | | Example | | | | | | | |
|---|---|---|---|---|---|---|---|---|---|
| | | 1 | 2 | 3 | 4 | 5 | 6 | 7 | 8 |
| | Boron | 0.508 | 0.421 | 0.421 | 0.208 | — | 0.508 | 0.508 | 0.508 |
| | Aluminum | — | — | — | — | 0.292 | — | — | — |
| Manufacturing method | | sequential method | sequential method | simultaneous method | sequential method | sequential method | sequential method | sequential method | sequential method |
| Reaction temperature (° C.) | | 300 | 300 | 300 | 300 | 300 | 260 | 280 | 320 |
| Mixed gas space velocity (L/L-catalyst/h) | | 6300 | 8400 | 8400 | 8400 | 6300 | 6300 | 6300 | 6300 |
| CO conversion rate (mol %) | | 31.0 | 28.1 | 23.1 | 36.5 | 18.4 | 12.7 | 21.1 | 37.7 |
| Selectivity (mol %) | Acetaldehyde | 48.6 | 52.8 | 56.3 | 48.9 | 28.4 | 79.2 | 68.3 | 24.0 |
| | Ethanol | 20.3 | 19.5 | 16.4 | 16.8 | 28.0 | 5.5 | 11.3 | 28.4 |
| | Total | 68.9 | 72.2 | 72.7 | 65.6 | 56.4 | 84.7 | 79.6 | 52.4 |
| Amount produced (g/L-catalyst/h) | Acetaldehyde | 309 | 388 | 356 | 466 | 107 | 198 | 283 | 177 |
| | Ethanol | 129 | 143 | 104 | 160 | 106 | 14 | 49 | 220 |
| | Total | 438 | 531 | 460 | 626 | 213 | 212 | 332 | 397 |

TABLE B2

| | | Comparative Example | | | | |
|---|---|---|---|---|---|---|
| | | 1 | 2 | 3 | 4 | 5 |
| Composition (molar ratio) | Rhodium | 0.708 | 0.500 | 0.708 | 0.708 | 0.708 |
| | Manganese | 0.194 | 0.250 | 0.194 | 0.194 | 0.194 |
| | Lithium | 0.098 | 0.250 | 0.098 | 0.098 | 0.098 |
| | Boron | — | — | — | — | — |
| | Aluminum | — | — | — | — | — |
| Manufacturing method | | simultaneous method | simultaneous method | simultaneous method | simultaneous method | simultaneous method |
| Reaction temperature (° C.) | | 300 | 300 | 260 | 280 | 320 |
| Mixed gas space velocity (L/L-catalyst/h) | | 6300 | 8400 | 6300 | 6300 | 6300 |
| CO conversion rate (mol %) | | 12.3 | 17.1 | 3.2 | 6.8 | 22.3 |
| Selectivity (mol %) | Acetaldehyde | 47.0 | 48.5 | 71.8 | 62.2 | 27.4 |
| | Ethanol | 23.2 | 13.4 | 8.5 | 13.8 | 29.7 |
| | Total | 70.2 | 61.9 | 80.3 | 76.0 | 57.0 |
| Amount produced (g/L-catalyst/h) | Acetaldehyde | 119 | 217 | 44 | 83 | 120 |
| | Ethanol | 58 | 60 | 6 | 19 | 136 |
| | Total | 177 | 277 | 50 | 102 | 256 |

As illustrated in Table B1, Examples 131 to 135 applicable to the present invention exhibited a CO conversion rate of 18.4 mol % or greater, and yielded a total amount of produced oxygenates (total of acetaldehyde and ethanol) of 213 g/L-catalyst/h or greater. In addition, in Examples B1 to B5, the amount of ethanol produced was 104 g/L-catalyst/h or greater.

Moreover, comparison of Examples B1 and B6 to B8 and Comparative Examples B1 and B3 to B5 reveals that, at any reaction temperature, the total amount of oxygenates produced in the example was higher than the total amount of oxygenates produced in the corresponding comparative example.

Comparison of Examples B1 and B5 and Comparative Example B1, in which the space velocity of the mixed gas was 6300 L/L-catalyst/h, reveals that, compared with Comparative Example 1, the total amount of oxygenates produced and the amount of ethanol produced was higher in Examples B1 and B5.

Further, comparison of Examples B2 to B4 and Comparative Example B2, in which the space velocity of the mixed gas was 8400 L/L-catalyst/h, reveals that, compared with Comparative Example B2, the total amount of oxygenates produced and the amount of ethanol produced was higher in Examples B2 to B4.

Based on these results it was evident that by applying the present invention, the total amount of oxygenates produced could be increased, meaning the oxygenates could be synthesized efficiently from the mixed gas.

Comparison of Example B2 and Example B3 reveals that, compared with Example B3 in which manufacturing was performed using the simultaneous method, Example B2 in which manufacturing was performed using the sequential method yielded increases in the total amount of oxygenates produced and the amount of ethanol produced.

The ethanol selectivity in Examples B1 and B8, in which the reaction temperature was set to 300 to 320° C., was 20.3 mol % or greater, which was higher than the ethanol selectivity in Examples B6 and B7, in which the reaction temperature was set to 260 to 280° C.

On the other hand, the acetaldehyde selectivity in Examples B6 and B7, in which the reaction temperature was set to 260 to 280° C., was 68.3 mol % or greater, which was higher than the acetaldehyde selectivity in Examples B1 and B8, in which the reaction temperature was set to 300 to 320° C.

Based on these results it was evident that by changing the reaction temperature, the selectivity for ethanol or acetaldehyde could be increased.

Example C1

First, 1.08 mL of an aqueous solution containing 0.0531 g of magnesium nitrate hexahydrate ($Mg(NO_3)_2 \cdot 6H_2O$) (the primary impregnating solution) was added dropwise to 1.0 g of a silica gel (specific surface area: 310 m$^2$/g, average pore diameter: 14 nm, pore volume: 1.1 cm$^3$/g) to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.061 g of rhodium chloride ($RhCl_3$), 0.0017 g of lithium chloride (LiCl) and 0.0159 g of manganese chloride tetrahydrate ($MnCl_2 \cdot 4H_2O$) (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/$SiO_2$, and Rh:Mn:Li:Mg=0.484:0.133:0.067:0.316 (molar ratio). In Table C1, the method for manufacturing the catalyst in this example is recorded as the "sequential method".

Example C2

First, 1.08 mL of an aqueous solution containing 0.0152 g of lanthanum nitrate hexahydrate ($La(NO_3)_3 \cdot 6H_2O$) (the primary impregnating solution) was added dropwise to 1.0 g of the silica gel to impregnate the silica gel (the primary impregnation step). The resulting mixture was dried at 110° C. for 3 hours (the primary drying operation), and then baked at 450° C. for 3 hours to obtain a primary support body (the primary baking operation, the above represents the primary support step). Subsequently, 1.08 mL of an aqueous solution containing 0.061 g of rhodium chloride, 0.0017 g of lithium chloride and 0.0159 g of manganese chloride tetrahydrate (the secondary impregnating solution) was added dropwise to the primary support body to impregnate the primary support body (the secondary impregnation step), and the resulting mixture was dried at 110° C. for 3 hours (the secondary drying operation) and then baked at 450° C. for 3 hours to obtain a catalyst (the secondary baking operation, the above represents the secondary support step).

The thus obtained catalyst had a rhodium support ratio of 3 mass %/$SiO_2$, and Rh:Mn:Li:La=0.655:0.180:0.091:0.074 (molar ratio). In Table C1, the method for manufacturing the catalyst in this example is recorded as the "sequential method".

Examples C3, C6 to C8

With the exception of dipping the primary support body in a 2 mol/L aqueous solution of ammonia for 6 hours, and subsequently drying the support body at 110° C. for 2 hours before supplying it to the secondary impregnation step, a catalyst was obtained in the same manner as Example C1.

The thus obtained catalyst had a rhodium support ratio of 3 mass %/$SiO_2$, and Rh:Mn:Li:Mg=0.484:0.133:0.067:0.316 (molar ratio). In Table C1, the method for manufacturing the catalysts in these examples is recorded as the "hydroxide method".

Example C4

With the exception of using 1.08 mL of an aqueous solution containing 0.061 g of rhodium chloride, 0.0062 g of lithium chloride and 0.0288 g of manganese chloride tetrahydrate as the secondary impregnating solution, a catalyst was obtained in the same manner as Example C3.

The thus obtained catalyst had a rhodium support ratio of 3 mass %/$SiO_2$, and Rh:Mn:Li:Mg=0.377:0.189:0.189:0.245 (molar ratio). In Table C1, the method for manufacturing the catalyst in this example is recorded as the "hydroxide method".

Example C5

With the exceptions of using 1.08 mL of an aqueous solution containing 0.158 g of magnesium nitrate hexahydrate as the primary impregnating solution, and using 1.08 mL of an aqueous solution containing 0.061 g of rhodium chloride, 0.0062 g of lithium chloride and 0.0288 g of manganese chloride tetrahydrate as the secondary impregnating solution, a catalyst was obtained in the same manner as Example C3.

The thus obtained catalyst had a rhodium support ratio of 3 mass %/$SiO_2$, and Rh:Mn:Li:Mg=0.253:0.126:0.126:0.495 (molar ratio). In Table C1, the method for manufacturing the catalyst in this example is recorded as the "hydroxide method".

Comparative Examples C1, C3 to C5

First, 1.08 mL of an aqueous solution containing 0.061 g of rhodium chloride, 0.0017 g of lithium chloride and 0.0159 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst.

The thus obtained catalyst had a rhodium support ratio of 3 mass %/$SiO_2$, and Rh:Mn:Li=0.708:0.194:0.098 (molar ratio). In Table C2, the method for manufacturing the catalysts in these examples is recorded as the "simultaneous method".

Comparative Example C2

First, 1.08 mL of an aqueous solution containing 0.061 g of rhodium chloride, 0.0062 g of lithium chloride and 0.0288 g of manganese chloride tetrahydrate was added dropwise to 1 g of the silica gel to impregnate the silica gel, and the resulting mixture was dried at 110° C. for 3 hours, and then baked at 450° C. for 3 hours to obtain a catalyst.

The thus obtained catalyst had a rhodium support ratio of 3 mass %/$SiO_2$, and Rh:Mn:Li=0.500:0.250:0.250 (molar ratio). In Table C2, the method for manufacturing the catalyst in this example is recorded as the "simultaneous method".

(Evaluation Method)

A 0.1 g sample of the catalyst from each example was packed in a circular cylindrical reaction tube formed from stainless steel having a diameter of 2 mm and a length of 15 cm, thus forming a reaction bed. The reaction bed was heated at 320° C. for 2.5 hours while hydrogen was passed through the reaction bed at normal pressure at a space velocity of 1200 L/L-catalyst/h, thereby subjecting the catalyst to a reduction treatment.

Subsequently, under conditions including the reaction temperature shown in Table C1 or C2 and a reaction pressure of 2 MPa, a mixed gas ($H_2$/CO ratio=2) was passed through the reaction bed at a space velocity shown in Table C1 or C2, and a synthesis gas containing oxygenates was manufactured.

The mixed gas was passed through the reaction bed for 3 hours, and the obtained synthesis gas was collected and analyzed by gas chromatography.

From the thus obtained data, the CO conversion rate (mol %), the ethanol and acetaldehyde selectivity values (mol %), and the amounts produced of ethanol and acetaldehyde (g/L-catalyst/h) were calculated. These results are shown in Tables C1 and C2. The amounts produced of ethanol and acetaldehyde are values that indicate the mass of product per unit volume of catalyst per unit of time.

In addition, comparison of Examples C3 and C6 to C8 and Comparative Examples C1 and C3 to C5 reveals that, at any reaction temperature, the total amount of oxygenates produced in the example was higher than the total amount of oxygenates produced in the corresponding comparative example.

Based on these results it was evident that by applying the present invention, the total amount of oxygenates produced could be increased, meaning the oxygenates could be synthesized efficiently from the mixed gas.

Examples C3 and C5 manufactured using the hydroxide method exhibited an increase in the total amount of oxygen-

TABLE C1

| | | Example | | | | | | | |
|---|---|---|---|---|---|---|---|---|---|
| | | 1 | 2 | 3 | 4 | 5 | 6 | 7 | 8 |
| Composition (molar ratio) | Rhodium | 0.484 | 0.655 | 0.484 | 0.377 | 0.253 | 0.484 | 0.484 | 0.484 |
| | Manganese | 0.133 | 0.180 | 0.133 | 0.189 | 0.126 | 0.133 | 0.133 | 0.133 |
| | Lithium | 0.067 | 0.091 | 0.067 | 0.189 | 0.126 | 0.067 | 0.067 | 0.067 |
| | Magnesium | 0.316 | — | 0.316 | 0.245 | 0.495 | 0.316 | 0.316 | 0.316 |
| | Lanthanum | — | 0.074 | — | — | — | — | — | — |
| Manufacturing method | | sequential method | sequential method | hydroxide method | hydroxide method | hydroxide method | hydroxide method | hydroxide method | hydroxide method |
| Reaction temperature (° C.) | | 300 | 300 | 300 | 300 | 300 | 260 | 280 | 320 |
| Mixed gas space velocity (L/L-catalyst/h) | | 6300 | 6300 | 6300 | 8400 | 8400 | 6300 | 6300 | 6300 |
| CO conversion rate (mol %) | | 21.8 | 17.3 | 23.8 | 33.3 | 38.8 | 8.3 | 16.7 | 30.9 |
| Selectivity (mol %) | Acetaldehyde | 45.9 | 46.7 | 42.8 | 42.3 | 27.1 | 49.5 | 48.3 | 33.2 |
| | Ethanol | 21.3 | 25.6 | 24.8 | 23.8 | 32.1 | 13.9 | 18.9 | 28.6 |
| | Total | 67.1 | 72.3 | 67.6 | 66.1 | 59.2 | 63.5 | 67.2 | 61.8 |
| Amount produced (g/L-catalyst/h) | Acetaldehyde | 205 | 166 | 200 | 368 | 275 | 81 | 158 | 201 |
| | Ethanol | 95 | 91 | 116 | 217 | 341 | 23 | 62 | 174 |
| | Total | 300 | 257 | 315 | 585 | 615 | 104 | 220 | 375 |

TABLE C2

| | | Example | | | | |
|---|---|---|---|---|---|---|
| | | 1 | 2 | 3 | 4 | 5 |
| Composition (molar ratio) | Rhodium | 0.708 | 0.500 | 0.708 | 0.708 | 0.708 |
| | Manganese | 0.194 | 0.250 | 0.194 | 0.194 | 0.194 |
| | Lithium | 0.098 | 0.250 | 0.098 | 0.098 | 0.098 |
| | Magnesium | — | — | — | — | — |
| | Lanthanum | — | — | — | — | — |
| Manufacturing method | | simultaneous method | simultaneous method | simultaneous method | simultaneous method | simultaneous method |
| Reaction temperature (° C.) | | 300 | 300 | 260 | 280 | 320 |
| Mixed gas space velocity (L/L-catalyst/h) | | 6300 | 8400 | 6300 | 6300 | 6300 |
| CO conversion rate (mol %) | | 12.3 | 17.1 | 3.2 | 6.8 | 22.3 |
| Selectivity (mol %) | Acetaldehyde | 47.0 | 48.5 | 71.8 | 62.2 | 27.4 |
| | Ethanol | 23.2 | 13.4 | 8.5 | 13.8 | 29.7 |
| | Total | 70.2 | 61.9 | 80.3 | 76.0 | 57.0 |
| Amount produced (g/L-catalyst/h) | Acetaldehyde | 119 | 217 | 44 | 83 | 120 |
| | Ethanol | 58 | 60 | 6 | 19 | 136 |
| | Total | 177 | 277 | 50 | 102 | 256 |

As illustrated in Table C1, Examples C1 to C5 applicable to the present invention exhibited a CO conversion rate of 17.3 mol % or greater, and yielded a total amount of produced oxygenates (total of acetaldehyde and ethanol) of 257 g/L-catalyst/h or greater. In addition, in Examples C1 to C5, the amount of ethanol produced was 91 g/L-catalyst/h or greater.

In contrast, Comparative Examples C1 and C2 which did not contain the component (D) had a CO conversion rate of 7.1 mol % or less.

ates produced compared with Examples C1 and C2 manufactured using the sequential method.

Example C4, which had higher proportions of Mn and Li than Example C3, exhibited a higher CO conversion rate than Example C3. Example C5, which had a higher proportion of Mg than Example C4, exhibited a higher CO conversion rate than Example C4, and a higher selectivity for ethanol.

The ethanol selectivity in Examples C1 and C8, in which the reaction temperature was set to 300 to 320° C., was 21.3 mol % or greater, which was higher than the ethanol selectivity in Examples C6 and C7, in which the reaction temperature was set to 260 to 280° C.

On the other hand, the acetaldehyde selectivity in Examples C6 and C7, in which the reaction temperature was set to 260 to 280° C., was 48.3 mol % or greater, which was higher than the acetaldehyde selectivity in Examples C1 and C8, in which the reaction temperature was set to 300 to 320° C.

Based on these results it was evident that by changing the reaction temperature, the selectivity for ethanol or acetaldehyde could be increased.

INDUSTRIAL APPLICABILITY

The catalyst for oxygenate synthesis according to the present invention is capable of efficiently synthesizing an oxygenate from a mixed gas of hydrogen and carbon monoxide, and can therefore be used favorably, for example, in synthesizing ethanol from a cellulose-based biomass.

DESCRIPTION OF THE REFERENCE SIGNS

1: Reaction tube
2: Reaction bed
3: Supply tube
4: Discharge tube
5: Temperature control unit
6: Pressure control unit
10: Manufacturing device
20: Mixed gas
22: Synthesis gas

The invention claimed is:

1. A method for manufacturing a catalyst for oxygenate synthesis for synthesizing an oxygenate from a mixed gas containing hydrogen and carbon monoxide, the method comprising:
supporting a component (D) on a carrier to form a primary support body, bringing an alkaline aqueous solution into contact with the primary support body, and subsequently supporting components (A) to (C) on the primary support body,
wherein:
the component (A) is rhodium,
the component (B) is manganese,
the component (C) is an alkali metal, and
the component (D) is a component (D1), component (D2) or component (D3), wherein the component (D1) is one or more substances selected from the group consisting of titanium, vanadium and chromium, the component (D2) is an element belonging to group 13 of the periodic table, and the component (D3) is one or more substances selected from the group consisting of magnesium and lanthanoids.

2. A method for manufacturing a catalyst for oxygenate synthesis for synthesizing an oxygenate from a mixed gas containing hydrogen and carbon monoxide, the method comprising:
supporting a component (D) on a carrier to form a primary support body, bringing an alkaline aqueous solution into contact with the primary support body, and subsequently supporting components (A) to (C) on the primary support body,
wherein the component (A) is rhodium, the component (B) is manganese, the component (C) is an alkali metal, and the component (D) is a component (D1), component (D2) or component (D3),
wherein the component (D1) is one or more substances selected from the group consisting of titanium, vanadium and chromium, the component (D2) is an element belonging to group 13 of the periodic table, and the component (D3) is one or more substances selected from the group consisting of magnesium and lanthanoids, and
wherein the catalyst for oxygenate synthesis is represented by formula (I) shown below:

$$aA \cdot bB \cdot cC \cdot dD \qquad (I),$$

wherein A represents the component (A), B represents the component (B), C represents the component (C), D represents the component (D), and each of a, b, c and d represents a molar fraction, wherein
$a+b+c+d=1$,
$a=0.05$ to $0.98$
$b=0.0005$ to $0.67$,
$c=0.0005$ to $0.51$, and
$d=0.002$ to $0.95$.

3. The method for manufacturing the catalyst for oxygenate synthesis according to claim 1, wherein the alkaline aqueous solution is an aqueous solution of ammonia.

4. The method for manufacturing the catalyst for oxygenate synthesis according to claim 2, wherein the alkaline aqueous solution is an aqueous solution of ammonia.

5. The method for manufacturing the catalyst for oxygenate synthesis according to claim 1, wherein the concentration of the alkaline aqueous solution is 0.1 to 3 mol/L.

6. The method for manufacturing the catalyst for oxygenate synthesis according to claim 2, wherein the concentration of the alkaline aqueous solution is 0.1 to 3 mol/L.

7. The method for manufacturing the catalyst for oxygenate synthesis according to claim 1, wherein the temperature of the alkaline aqueous solution is 15 to 30° C.

8. The method for manufacturing the catalyst for oxygenate synthesis according to claim 2, wherein the temperature of the alkaline aqueous solution is 15 to 30° C.

* * * * *